(12) United States Patent
Wilson et al.

(10) Patent No.: US 11,020,547 B2
(45) Date of Patent: Jun. 1, 2021

(54) DRY POWDER INHALER WITH BLISTER BURSTING DEVICE

(71) Applicant: Vectura Delivery Devices Limited, Chippenham (GB)

(72) Inventors: Peter Wilson, Cambridge (GB); Roger Clarke, Cambridge (GB); Liam McGuinness, Cambridge (GB)

(73) Assignee: VECTURA DELIVERY DEVICES LIMITED, Wiltshire (GB)

( * ) Notice: Subject to any disclaimer, the term of this patent is extended or adjusted under 35 U.S.C. 154(b) by 381 days.

(21) Appl. No.: 16/303,764

(22) PCT Filed: May 25, 2017

(86) PCT No.: PCT/EP2017/062713
§ 371 (c)(1),
(2) Date: Nov. 21, 2018

(87) PCT Pub. No.: WO2017/203021
PCT Pub. Date: Nov. 30, 2017

(65) Prior Publication Data
US 2020/0316322 A1   Oct. 8, 2020

(30) Foreign Application Priority Data
May 25, 2016   (EP) .................................... 16171390

(51) Int. Cl.
*A61M 15/00* (2006.01)
(52) U.S. Cl.
CPC .... *A61M 15/0031* (2014.02); *A61M 15/0021* (2014.02); *A61M 15/0051* (2014.02); *A61M 15/0056* (2014.02); *A61M 2202/064* (2013.01)
(58) Field of Classification Search
CPC .............. A61M 15/00; A61M 15/0026; A61M 15/0028; A61M 15/003; A61M 15/0031;
(Continued)

(56) References Cited

U.S. PATENT DOCUMENTS

| 2005/0121032 A1 | 6/2005 | Nilsson et al. |
| 2007/0137645 A1* | 6/2007 | Eason ............... A61M 15/0025 128/203.15 |

(Continued)

FOREIGN PATENT DOCUMENTS

| CN | 1867369 | 11/2006 |
| CN | 104225740 | 12/2014 |

(Continued)

*Primary Examiner* — Joseph D. Boecker
(74) *Attorney, Agent, or Firm* — Barnes & Thornburg LLP; Ryan P. Cox

(57) ABSTRACT

A multi-dose dry powder inhaler with a blister folding device is provided. The inhaler comprises a housing containing a blister strip, and a blister opening device. The blister strip comprises a plurality of individual blisters, each blister containing a dose of medicament for inhalation by a user. The blister opening device comprising a blister support element for supporting one of said blisters, and a blister folding element co-operable with the blister support element, the blister folding element and the blister support element being movable relative to each other between a first position, permitting movement of said blister into or onto the blister support element, and a second, burst, position in which the blister folding element has co-operated with the blister support element. Movement from the first position to the second position causes two spaced apart portions of said blister to each fold relative to the remainder of the blister to produce two spaced apart openings, each opening extending along the circumference of the blister bowl, beginning and terminating at points located on the fold line No piercing of the blister at any stage is required.

11 Claims, 7 Drawing Sheets

(58) Field of Classification Search
CPC .......... A61M 15/0033; A61M 15/0035; A61M 15/0038; A61M 15/0041; A61M 15/0045; A61M 15/0051; A61M 15/0056; A61M 11/00
See application file for complete search history.

(56) References Cited

U.S. PATENT DOCUMENTS

2008/0116220 A1* 5/2008 Pocock ............. A61M 15/0041
222/80
2009/0090362 A1* 4/2009 Harmer ............. A61M 15/0033
128/203.21

FOREIGN PATENT DOCUMENTS

| | | |
|---|---|---|
| GB | 2407042 A | 4/2005 |
| GB | 2485858 A | 5/2012 |
| TW | 201408340 | 3/2014 |
| WO | 2005037353 A1 | 4/2005 |
| WO | 2009083244 | 7/2009 |
| WO | 2009083244 A2 | 7/2009 |
| WO | 2010086285 A2 | 8/2010 |
| WO | 2013175176 A1 | 11/2013 |
| WO | 2014006135 A2 | 1/2014 |
| WO | 2016083102 A1 | 6/2016 |

* cited by examiner

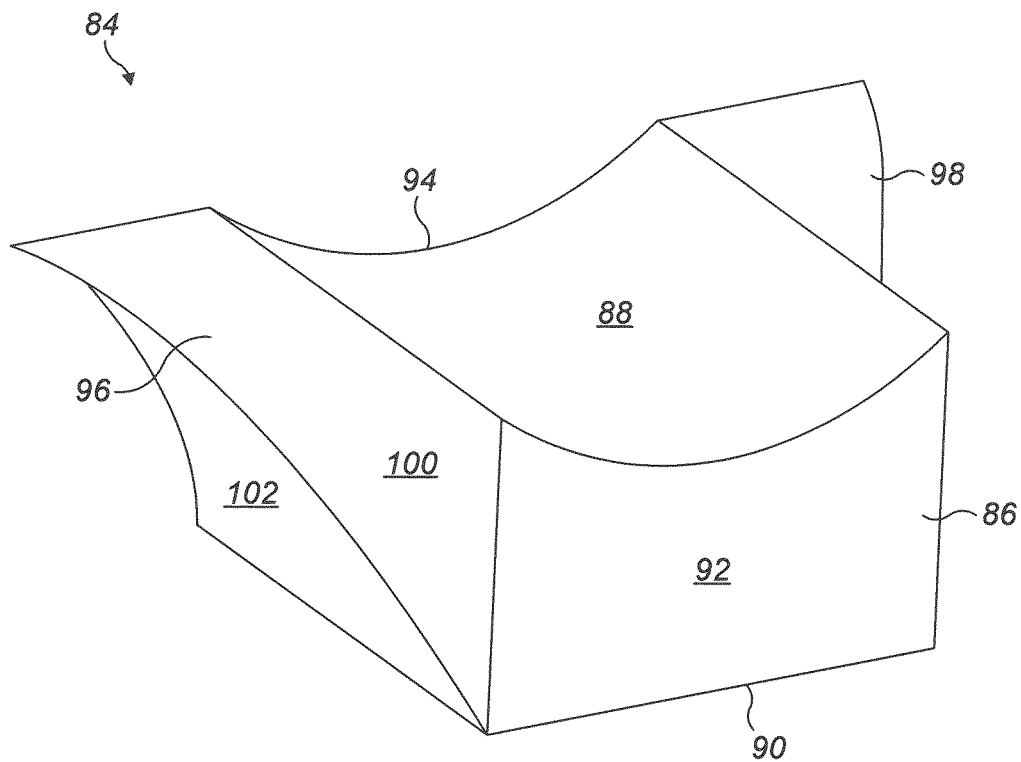
FIG. 12
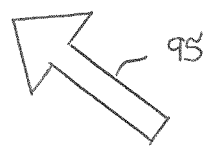

DRY POWDER INHALER WITH BLISTER BURSTING DEVICE

CROSS-REFERENCE TO RELATED APPLICATIONS

This application is a United States national stage of International Application No. PCT/EP2017/062713, filed May 25, 2017, which was published as International Publication No. WO 2017/203021, and which claims benefit of European Patent Application No. 16171390.4, filed May 25, 2016, the entire contents of which are hereby expressly incorporated herein by reference.

The present invention relates to a blister opening device for a multi dose dry powder inhalation device. In particular, it relates to a blister bursting device for popping or bursting open the lid of a blister that contains an individual dose of medicament for inhalation by a user of the inhalation device.

Oral or nasal delivery of a medicament using an inhalation device is a particularly attractive method of drug administration as these devices are relatively easy for a patient to use discreetly and in public. As well as delivering medicament to treat local diseases of the airway and other respiratory problems, they have also been used to deliver drugs to the bloodstream via the lungs, thereby avoiding the need for hypodermic injections.

It is common for dry powder formulations to be pre-packaged in blisters, each of which contains a single dose of powder which has been accurately and consistently measured. The blister protects each dose from the ingress of moisture and penetration of gases such as oxygen in addition to shielding the dose from light and UV radiation, all of which can have a detrimental effect on the medicament and on the operation of an inhaler used to deliver the medicament to a patient.

A blister pack generally comprises a base having one or more spaced apart cavities (also known as blister bowls) defining blisters to receive individual doses of medicament and a lid in the form of a generally planar sheet that is sealed to the base except in the region of the cavities. The base material is typically a laminate comprising a polymer layer in contact with the drug, a soft tempered aluminium layer and an external polymer layer. The aluminium provides the moisture and oxygen barrier, whilst the polymer aids adhesion of the aluminium to the heat seal lacquer and provides a relatively inert layer in contact with the drug. Soft tempered aluminium is ductile so that it can be "cold formed" into a blister shape. It is typically 45 µm thick. The outer polymer layer provides additional strength and toughness to the laminate.

The lid material is typically a laminate comprising a heat seal lacquer, a hard rolled aluminium layer and an external lacquer layer. The heat seal lacquer layer bonds to the polymer layer of the base foil laminate during heat-sealing to provide a seal around the top of the blister cavity. The hard temper foil is relatively frangible to enable it to be pierced easily by a piercing element forming part of an inhalation device, to create one or more openings in the lid. These openings enable air or gas to flow through the blister, thereby entraining the dry powder and causing it to be removed from the blister. The powder can then be deagglomerated to form a respirable cloud and made available for inhalation by the user.

Inhalation devices that receive a blister pack or strip of blisters are known. Actuation of the device causes a mechanism to index and pierce a blister so that when the device is used, air is drawn through the blister entraining the dose, which is then carried out of the blister through the device and via the patient's airway down into the lungs. One such device is known from one of the Applicant's own European patent No. 1684834B1.

The airflow can be created by inhalation of the user. Such inhaler devices are generally known as passive devices. Alternatively, the inhaler may include a source of energy such as a mechanical pump or canister of pressurised gas to generate pressure or suction. The air or gas flow in these active devices can potentially be greater than that in a passive device, and more repeatable. This can give better and more consistent blister emptying.

Hitherto, much development work has been focused on piercing as a mode of blister opening. It is now well understood that it is difficult to control the size and configuration of the opening in a blister lid caused by piercing because the foil may not always tear or burst in a consistent way. Furthermore, the means by which the blister is pierced is of critical importance in the performance of a dry powder inhalation device.

It is common for problems to occur in dry powder inhalers that use piercers as means for opening blisters because, when the lid is pierced, foil flaps are formed that are pushed into the blister. These can either trap powder in the blister or obscure the opening. It will be appreciated that it is beneficial to form a large opening in the blister lid to enable a sufficient flow of air through the blister, and to enable the removal of agglomerates that may have formed in the powder during storage. However, a large opening in the blister means that the foil flaps are large and so are more likely to trap powder and hinder airflow. Furthermore, more powder may be trapped depending upon the orientation in which the device is being held when piercing takes place.

Trapped powder and a hindered airflow are the focus of WO2014/006135 from Glaxo Group Limited. It discloses a dry powder inhaler for receiving a single blister onto a blister seat. The inhaler housing is made up of a base and a lid which are pivotable relative to one another between open and closed positions, the lid supporting a punch and the base containing the aforementioned blister seat. The punch comprises an upstream blade and a downstream blade, each blade having a curved free cutting edge.

In use, the housing lid is moved from the open position, in which a blister may be placed on the blister seat, to the closed position, in which it abuts the housing base. In doing so, two apertures are created in the lid material. Once the initial piercing of the lid has taken place, and this occurs sequentially, flaps are formed in the lid material as the user continues to close the lid against the housing base. A final movement of the lid relative to the housing base causes the piercing blades to further enlarge the apertures formed in the lid.

In this prior art inhaler, the foil flaps are unusually considered advantageous as, together with an annular overhang about the blister bowl created during the opening process, they create a torturous flow path for the powder-laden airflow to follow as it exits the blister bowl. This torturous flow path is desirable because it assists with powder deagglomeration before inhalation.

In contrast to WO2014/006135, the present invention seeks to provide a blister opening device adapted for multi dose inhalers, one that ensures a smooth flow of air through an opened blister whilst it is still part of a blister strip. It avoids potentially expensive powder becoming trapped behind foil flaps created in the blister lid, which traditionally occurs when a blister lid is opened by piercing.

According to the invention, there is provided a dry powder inhaler comprising a housing defining a chamber, a blister strip having a plurality of blisters each containing a dose of medicament for inhalation by a user, each blister comprising a blister lid attached to a blister bowl, the blister strip being inside the chamber, an actuator, an indexing system to sequentially move each blister into a blister opening position in response to movement of the actuator, a mouthpiece through which a dose of medicament is inhaled by a user, and a blister opening device, the blister opening device comprising a blister support element for supporting one of said blisters, and a blister folding element co-operable with the blister support element, the blister folding element and the blister support element being movable relative to each other between a first position, permitting movement of said blister into or onto the blister support element, and a second, burst, position in which the blister folding element has co-operated with the blister support element, movement from the first position to the second position causing two spaced apart portions of said blister to each fold relative to the remainder of the blister along a respective fold line and against the blister support element to produce two spaced apart openings, each opening extending along the circumference of the blister bowl, beginning and terminating at points located on the fold line such that, when a user inhales through the mouthpiece, an airflow through the blister via the two openings is generated to entrain the dose contained therein and carry it out of the blister and via the mouthpiece into the user's airway.

The key advantage of this invention is that when the blister is burst open, two unobstructed openings are created. This facilitates a rapid and unhindered exit of powder from the blister, which improves the emitted dose of the inhaler. This mode of opening blisters is particularly useful for spray dried formulations and biologics, which currently represent the cutting edge of pharmaceutical research. Such powders can be expensive and a minimal retention of powder within the blister bowl after opening is highly desirable.

Preferably, the blister folding element and the blister support element are slidable relative to each other.

Preferably, the indexing system comprises a blister strip drive member rotatably mounted in the chamber.

Preferably, the blister strip drive member incorporates the blister support element.

The blister folding element may comprises two pairs of spaced apart fold members configured to slide adjacent to the blister strip drive wheel.

Preferably, the blister strip drive member comprises an indexing wheel, the indexing wheel comprising a plurality of blister seats to support a blister bowl, said plurality of seats being equi-angularly spaced apart about an axis of rotation of the blister strip drive member.

Preferably, each blister seat comprises a central portion which has a truncated geometric shape, each fold line being one edge of truncation.

Optionally, a longitudinal extent of each blister seat is arranged perpendicularly to the direction of travel of the blister strip during indexing.

Each blister seat may incorporate a raised feature to cause an indentation at the base of the blister bowl for internally pressurising the blister. By placing an indentation in the blister bowl (caused by the raised feature), this pressurises the internal contents of the sealed blister just prior to opening which helps the lid of the blister to pop open during the opening process. The indentation may be a dimple or a convex channel extending along the length of the blister bowl.

In one embodiment, the actuator is an actuating lever pivotally mounted to the housing. As such, the actuating lever may be operable to cause blister indexing during a first portion of its stroke, and to cause blister folding during a second and subsequent portion of its stroke. In an alternative embodiment, the actuator is a cap pivotally mounted to the housing. The device is thus a cap operated inhaler.

A deagglomeration chamber for deagglomerating powder from the opened blister may be provided. The deagglomeration chamber, also known as a cyclone chamber, may be located within the mouthpiece. The chamber has an inlet at one end for the flow of drug laden air into the chamber from a burst blister and an outlet at its opposite end for the flow of drug laden air out of the mouthpiece and into a patient's airway. Ideally, the chamber has a longitudinal axis that extends between the inlet and the outlet.

Cyclone chambers, also known as deagglomeration chambers, help to break up large agglomerates formed during the blister filling process and subsequent storage. Agglomerates are broken up by impact or collision with the internal surfaces of the cyclone chamber. Agglomeration formation is exacerbated in particularly cohesive formulations. Spray dried formulations and biologics have been found to be cohesive by nature too. A cyclone chamber is particularly important for use in combination with this mode of opening blisters, since the inhaler is intended to be used to dispense spray dried formulations and biologics.

Additionally, cyclone separation using a cyclone chamber is a common method of removing particulates from an air stream. As the air flows in a rotating pattern, large agglomerates have too much inertia to follow the tight curve of the air stream and therefore impact the wall of the cyclone chamber.

The cyclone geometry and flow rate determine the agglomerate size which will remain in the cyclone. No two formulations have the same properties and therefore the size of the cyclone chamber needs to be designed individually for each formulation.

Optionally, the chamber comprises at least one bypass air inlet for the flow of clean air into the chamber to interact with the drug laden air flowing between the inlet and the outlet. Preferably, the bypass air inlet(s) meets the chamber at a tangent so that a cyclonic airflow is generated from clean air around the drug laden airflow. Agglomerates are formed due to cohesive forces between particles, but these forces also occur between particles and surfaces. Testing has shown that the deposition of fine particles on surfaces is a significant risk and with a biologic compound, the retention of powder in the device could lead to complications. Creating a cyclonic airflow reduces this risk.

Preferably, the or each bypass air inlet is arranged at or near the chamber outlet.

The dry powder inhaler may further comprise an unfolding member to return folded portions of an opened blister back to their original unfolded condition. The advantage of the unfolding member is that by unfolding the folded portions of each opened blister, the compactness of the used blister strip as it is gradually being recoiled within the housing is improved. An unfolding member facilitates tighter recoil, thereby reducing the internal capacity required by the used blister strip.

Preferably, the blister strip incorporates two longitudinal edges, each edge comprising a series of spaced apart fold ears which extend laterally outwardly. The fold ears have been found to make the blister strip easier to pop open, though they are not considered essential to the invention.

An embodiment of the invention will now be described, by way of example only, with reference to the accompanying drawings, in which:—

FIG. 12 shows an unfolding member.

Figure 1:
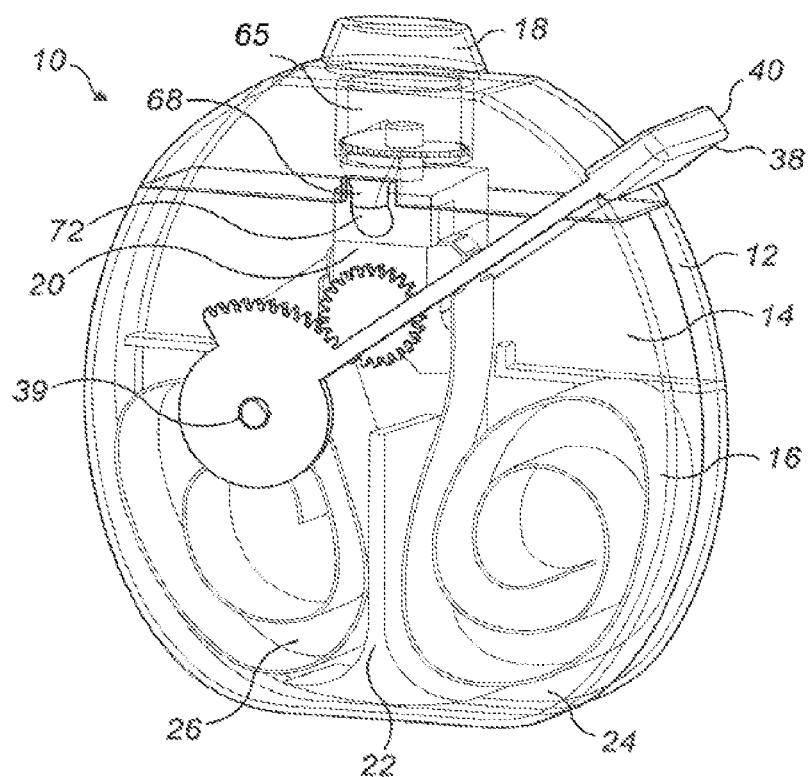
FIG. 1 shows a front view of a lever operated embodiment of the inhaler according to the invention, in which the lever is in a raised position, and the inhaler is in a rest condition.
Figure 2:
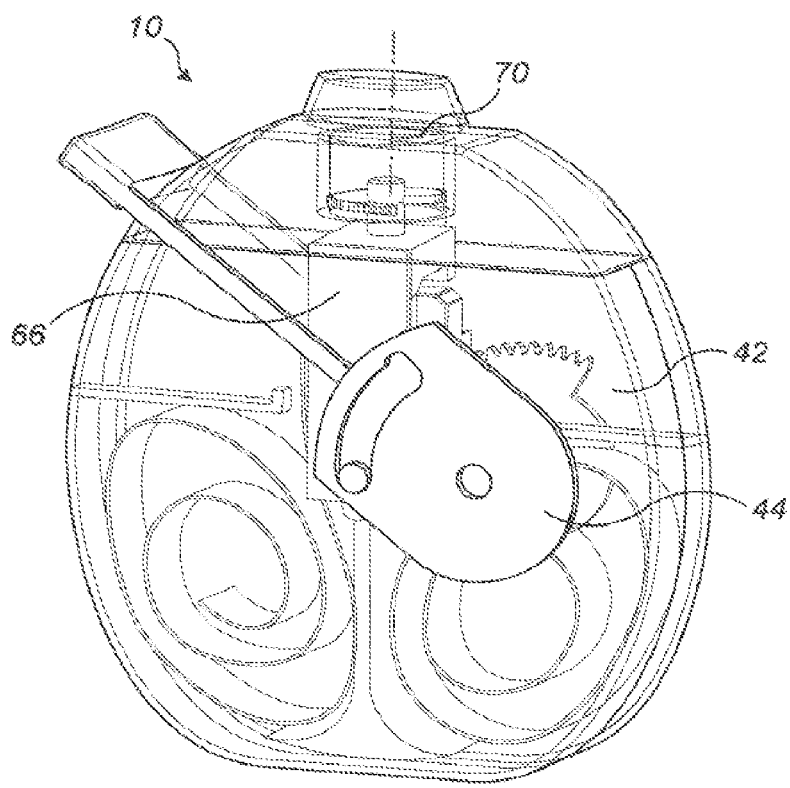
FIG. 2 shows a rear view of the inhaler of FIG. 1.
Figure 3:
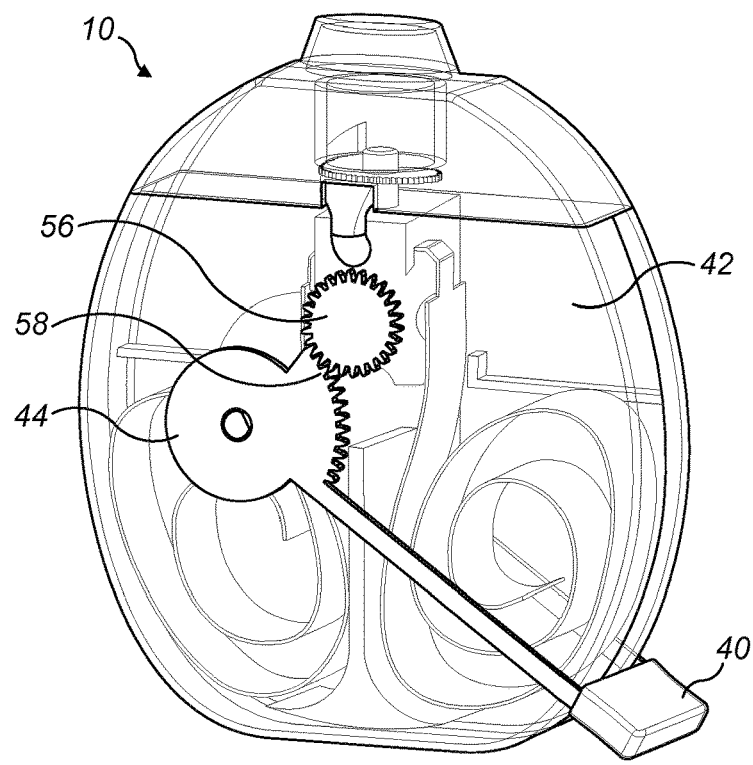
FIG. 3 shows a front view of the inhaler, in which the lever is in a lowered position, and the inhaler is in an active condition, ready for inhalation.

Referring firstly to FIGS. 1 to 4, a multi-dose dose dry powder inhaler is indicated generally at 10. The inhaler 10 comprises a housing 12 defining a chamber 14, a blister strip 16 inside the chamber 14, a mouthpiece 18 through which a dose of medicament is inhaled by a user, an actuator, an indexing system to sequentially move each blister into a blister opening position 20 in response to movement of the actuator, and a blister opening device.

The chamber 14 is essentially divided into two compartments, separated by a movable wall 22. Such a wall 22 has been described in Applicant's own WO 2012/069854. Before first use of the inhaler 10, a coil of unused blister strip 16 is stored inside a first compartment 24. As the blister strip 16 is advanced by the indexing system, the blister strip 16 uncoils and progresses towards the blister opening position 20. Subsequent indexing causes the opened (i.e. used) portion of the blister strip 16 to move into a second compartment 26, and the used portion of the blister strip 16 to gradually recoil. The movable wall 22 is slidable within the chamber 14 to automatically adjust the relative capacity of the first and second compartments 24, 26 as the diameter of the unused portion of the blister strip 16 coil decreases and the diameter of the used portion of the blister strip 16 coil increases. Alternatively, the movable wall 22 may be pivotally mounted within the chamber 14.

Figure 5:
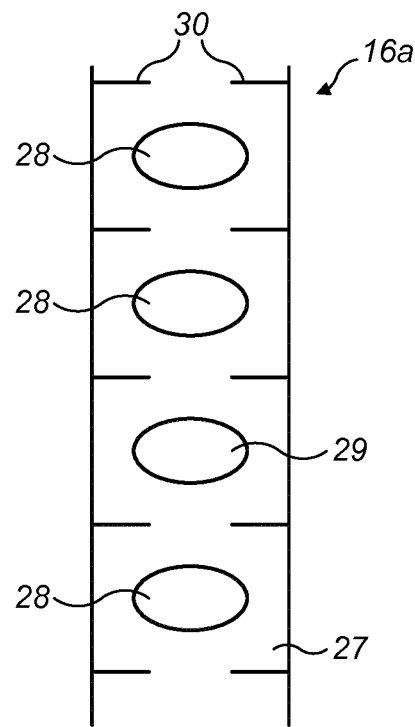
FIG. 5 shows a plan view of a first embodiment of the blister strip.
Figure 6:
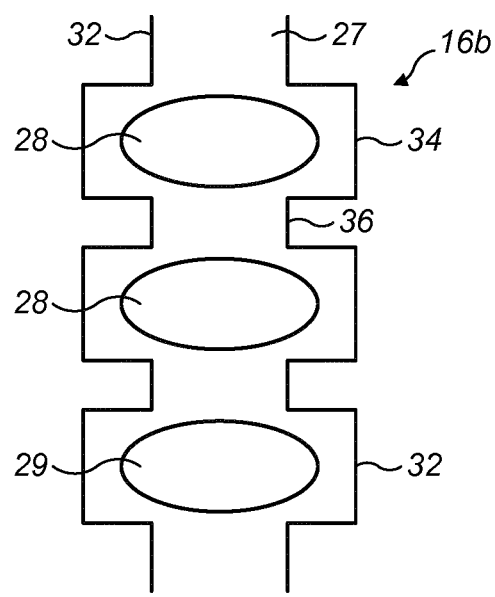
FIG. 6 shows a plan view of a second embodiment of the blister strip.

The blister strip 16 comprises a plurality of blisters 28 (see FIGS. 5 and 6), each containing an individual dose of medicament for inhalation by a user. Each blister 28 comprises a blister lid 27 attached to a blister bowl 29. Preferably the blister bowl 29 is oval, but other geometric shapes may be used. Exemplary blister strips are shown in FIGS. 5 and 6. Either configuration of blister strip 16 may be used, but the one shown in FIG. 6 is considered to work better in practice.

In FIG. 5, blister strip 16a incorporates two lines of weakness 30 between adjacent blisters 28. Each line of weakness 30 extends partially across the breath of the blister strip 16a. Alternatively, a single line of weakness 30 may extend across the full breath of the blister strip 16a. The line of weakness 30 is typically formed by scoring into the uppermost layer of the blister strip 16a, but not other layers below, for example using a laser. By not affecting the layers below, the moisture protection of the blister strip 16a is retained. One way of achieving such a line of weakness 30 has been described in the Applicant's own WO 2006/108876. Other variations on the number and length of the or each line of weakness 30 are envisaged.

In FIG. 6, blister strip 16b has two longitudinal edges 32, each edge 32 comprising a series of spaced apart fold ears 34 which extend laterally outwards. In other words, in plan view, each edge resembles a square tooth wave profile. There is a notch 36 adjacent to each fold ear 34. The notch 36 extends into each blister strip 16b such that it laterally passes the end of the blister bowl 29. As such, a virtual fold line extends longitudinally from recess to recess, bisecting the end of the blister bowl 29.

The mouthpiece 18 is mounted to the housing 12. The mouthpiece 18 does not move relative to the housing 12.

The actuator is operable to cause indexing of the blister strip 16 and subsequently blister 28 opening, as will be described in further detail below. In this embodiment, the actuator is an actuating lever 38 pivotally mounted to the housing 12 about a first axis of rotation 39. Preferably, the actuating lever 38 comprises an actuating button 40 that extends across the outside of the housing 12 between opposing side wall surfaces 42 of the housing 12, and a plate-like portion 44 extending from each end of the actuating button 40 across respective side wall surfaces 42 on the outside of the housing 12.

Alternatively the actuator may comprise a cap pivotally mounted to the housing 12. Such a cap works in a similar way as the actuating lever 38, but with the resulting inhaler 10 being cap operated as opposed to lever operated. This simplifies operation of the inhaler 10 for the user as it removes the step of opening a passive cover or cap (not shown) in order to operate the actuating lever 38.

Figure 7:
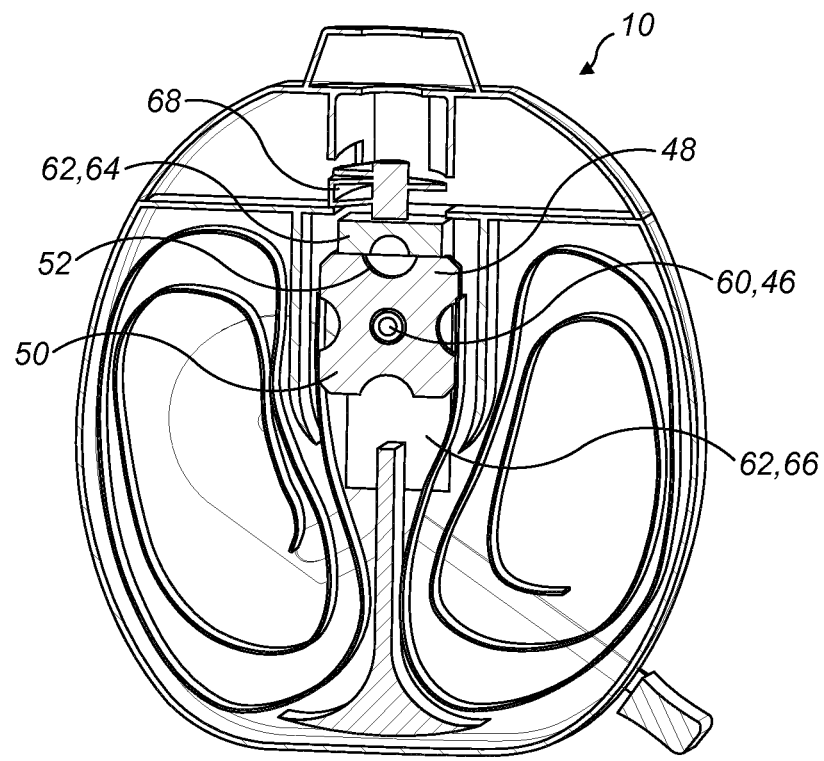
FIG. 7 shows a front cross-sectional view of the inhaler of FIG. 3 with certain features omitted for clarity.
Figure 8:
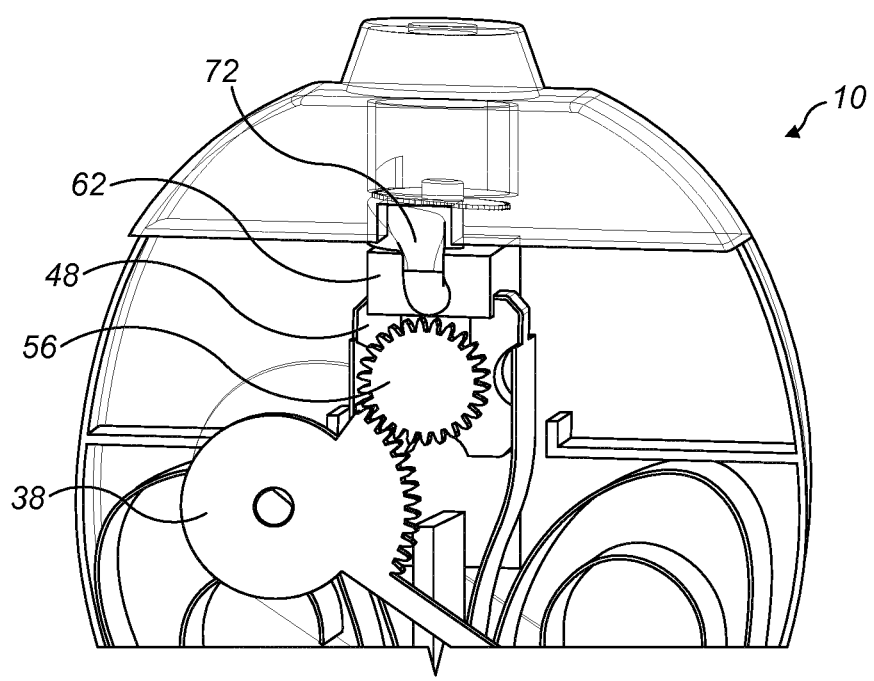
FIG. 8 shows an enlarged view of the blister support element, and the actuating lever.

The indexing system comprises a blister strip drive member rotatably mounted in the chamber 14 about a second axis of rotation 46. The blister strip drive member comprises an indexing wheel 48 (best seen in FIG. 7) having two radially extending and spaced apart major surfaces 50. These opposing major surfaces 50 are planar. The indexing wheel 48 comprises a plurality of blister seats 52 to support a blister bowl 29. The blister seats 52 are equi-angularly spaced apart about the axis of rotation 46 of the blister strip drive member. The blister seats 52 are located between the two major surfaces 50. A longitudinal extent of each blister seat 52 is arranged perpendicularly to the direction of travel of the blister strip 16 during indexing. Each blister seat 52 comprises a central portion (not shown) which has a truncated geometric shape, and two spaced apart lines of truncation 54 (best seen in FIG. 9). Each line of truncation 54 coincides with a respective peripheral edge of the one of the two major surfaces 50. The shape of the central portion complements the shape of the blister bowl 29 such that a blister bowl 29 is at least partially nestable within one of the blister seats 52.

Optionally, each blister seat 52 may incorporate a raised feature to cause an indentation at the base of the blister bowl 29 for internally pressurising the blister 28 prior to opening.

The blister strip drive member also comprises a drive gear 56, and the actuating lever 38 comprises a drive gear element 58. The drive gear element 58 is preferably formed on one of the plate-like portions 44 of the actuating lever 38. The drive gear 56 is connected to the indexing wheel 48 via a shaft 60 that extends through aperture in a side wall surface 42 of the housing 12. The shaft 60 is coaxial with the indexing wheel 48 on the second axis of rotation 46. The drive gear 56 is cooperable with the drive gear element 58 via meshing engagement. The drive gear 56 and drive gear element 58 are disposed on the outside of the housing 12 remote from the chamber 14. They are mounted underneath a cap or cover (not shown) such that they are not visible to the user during normal use.

The blister opening device comprises a blister support element for supporting one of the blisters of the blister strip, and a blister folding element 62, which is co-operable with the blister support element. The blister folding element 62 and the blister support element are movable relative to each other between a first position, permitting movement of said blister into or onto the blister support element during indexing, and a second, burst, position in which the blister folding element 62 has co-operated with the blister support element.

Preferably, the blister folding element 62 is movable relative to the blister support element. More preferably, the blister folding element 62 is slidably movable relative to the blister support element, as it is in this embodiment.

In this embodiment, the blister folding element 62 comprises two pairs of spaced apart fold members 64. One pair of said fold members 64 slides contiguous one of the two major surfaces 50 of the indexing wheel 48. The other pair of said fold members 64 slides contiguous the other of the two major surfaces 50 of the indexing wheel 48. Each of the fold members 64 is spaced apart within a pair to allow space for the lid 27 of the blister 28 to move into during popping/bursting. The two pairs of fold members 64 are connected to an elongate support 66 which is slidably mounted within the housing 12.

Figure 9:
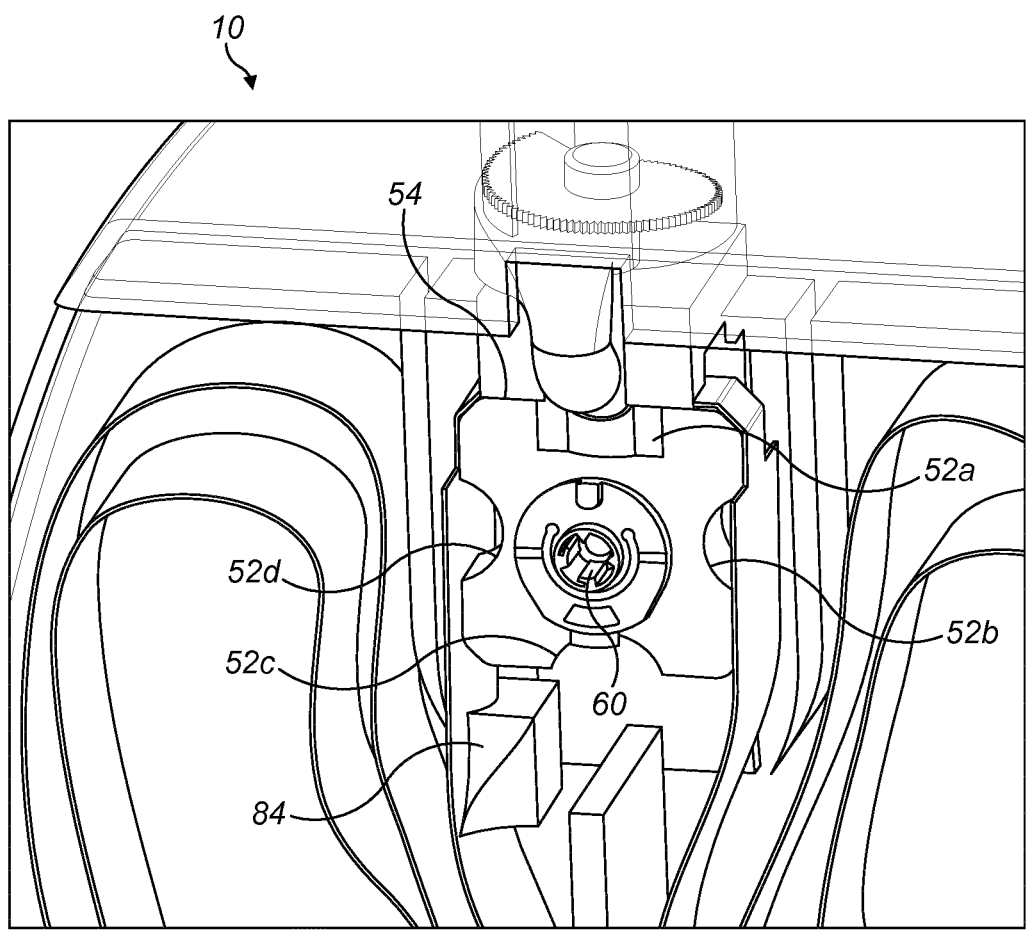
FIG. 9 shows an enlarged view of the blister support element at the moment blister folding occurs.

The blister support element incorporates the indexing wheel 48 and the aforementioned plurality of blister seats 52. There are four blister seats 52a, 52b, 52c, 52d (see FIG. 9), though more or less blister seats 52 may be used instead. The indexing wheel 48 is square-like, and the four blister seats 52a, 52b, 52c, 52d are situated at ninety degree intervals about the axis of rotation 46 of the indexing wheel 48. For simplicity, in the following explanation the reference view is a front view of the inhaler. During use, the indexing wheel 48 rotates in an anti-clockwise direction about the axis of rotation 46. Blister seat 52a at position zero degrees, this being the blister seat 52 nearest the mouthpiece 18 in FIG. 9, is in the blister opening position 20. Blister seat 52b at position ninety degrees, as measured clockwise from the zero position, contains an unopened blister 28 (not shown). Blister seat 52c is devoid of any blister 28. Blister seat 52d positioned at two hundred and seventy degrees, again measured clockwise from the zero position, contains an opened blister 28 (not shown).

A deagglomeration chamber 65 is mounted within the mouthpiece 18 and is used to deagglomerate powder from the opened blister 28. The position of the deagglomeration chamber 65 relative to the mouthpiece 18 is fixed. The deagglomeration chamber 65 has an inlet 68 at one end for the flow of drug laden air into the chamber 14 from a burst blister 28 and an outlet at its opposite end for the flow of drug laden air out of the mouthpiece 18 and into a patient's airway. The deagglomeration chamber 65 has a longitudinal axis 70 that extends between the inlet 68 and the outlet. Typically, drug laden air swirls about the longitudinal axis 70 during inhalation.

An airflow conduit 72 is located proximate the blister opening position 20. This airflow conduit 72 is telescopic, and can be extended and retracted as required.

The airflow conduit 72 connects the blister folding element 62 to the deagglomeration chamber 65. One end of the airflow conduit 72 is in fluid communication with the blister folding element 62 at or near the blister opening position 20. The other end of the airflow conduit 72 is in fluid communication with the inlet 68 of the deagglomeration chamber 65. The deagglomeration chamber 65 does not move with the blister folding element 62. Thus, when the blister folding element 62 is in the first position for blister indexing, the airflow conduit 72 is in a retracted condition. When the blister folding element 62 is in the second position for blister folding, the airflow conduit 72 is in an extended condition.

Figure 4:
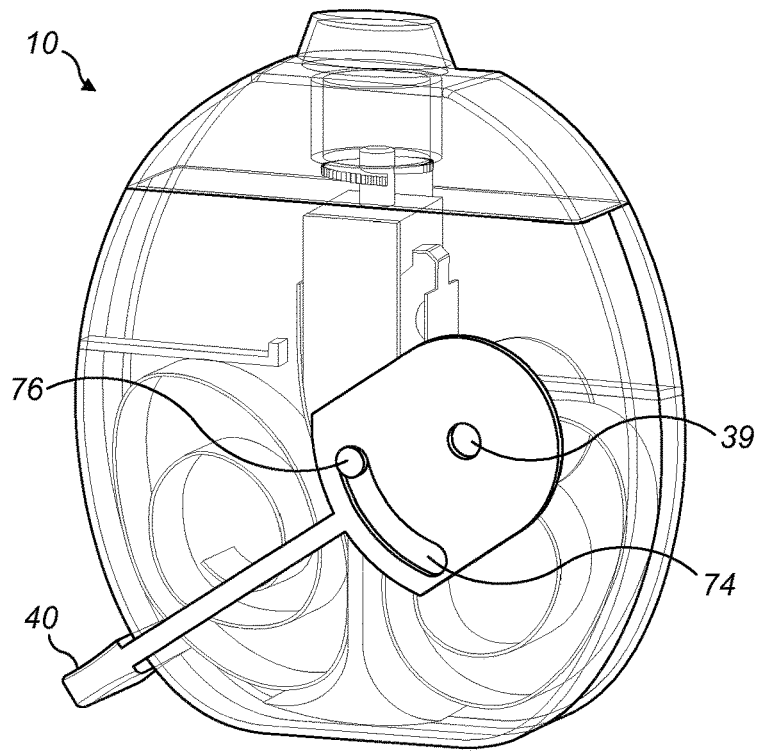
FIG. 4 shows a rear view of the inhaler of FIG. 3.

As best seen in FIG. 4, the actuating lever 38 has a drive cam surface 74 and the blister folding element 62 has a drive cam element 76. The drive cam surface 74 stands proud from the elongate support 66 of the blister folding element 62. The drive cam element 76 and the drive cam surface 74 are cooperable with each other in response to rotation of the actuating lever 38 so that the blister folding element 62 slides within the housing 12. Such movement of the blister folding element 62 occurs only after blister indexing has taken place.

The actuating lever 38 is operable to cause blister indexing during a first portion of its stroke in a first direction (i.e. downwards), and to cause blister folding during a second and subsequent portion of its stroke in the first direction. During the first portion of the stroke, drive gear 56 and drive gear element 58 cooperate to cause the indexing wheel 48 to rotate through ninety degrees. Drive cam element 76 slides freely within the drive cam surface 74 (se FIG. 2). During the second portion of the stroke, due to the presence of a drive coupling member (not shown), such as the one described in Applicant's own EP2254632, movement of the actuating lever 38 is disengaged from rotation of the indexing wheel 48. Therefore, further indexing is prevented. Drive cam element 76 abuts one end of the drive cam surface 74 such that further movement of the actuating lever 38 pulls the blister folding element 62 downwards (see FIG. 4). During the return stroke when the actuating lever 38 moves in a second opposing direction (i.e. upwards), neither indexing nor blister folding occurs. The blister folding element 62 is returned to its first position because the drive cam element 76 abuts the opposing end of the drive cam surface 74. Reverse indexing does not occur due to the drive coupling member.

In preparation for inhalation, movement of the blister folding element 62 from the first position (for example, see demonstration jig 78 in FIG. 10) to the second position (for example, see FIG. 11) causes two spaced apart portions of the blister 28 to each fold relative to the remainder of the blister 28 along a respective fold line 79 and against the blister support element. Each fold line 79 derives from one edge of truncation of the aforementioned truncated geometric shape.

This produces two spaced apart openings 80, 82, each opening 80, 82 extending along the circumference of the blister bowl 29, beginning and terminating at points located on the fold line 79. No piercing or puncturing is required at any time.

Figure 10:
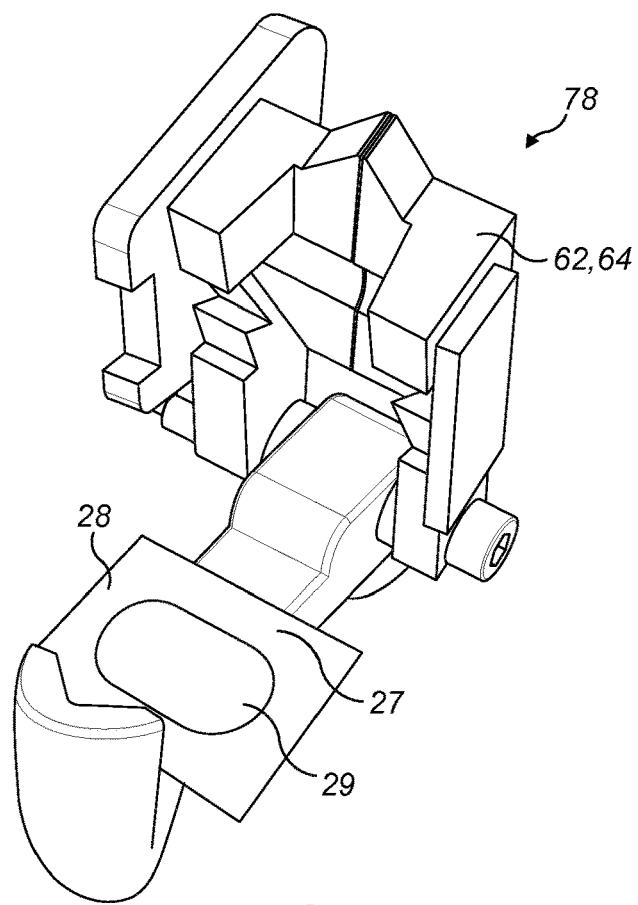
FIG. 10 shows a prototype jig for a unit dose device before blister opening, to demonstrate the effect of folding on the blister.
Figure 11:
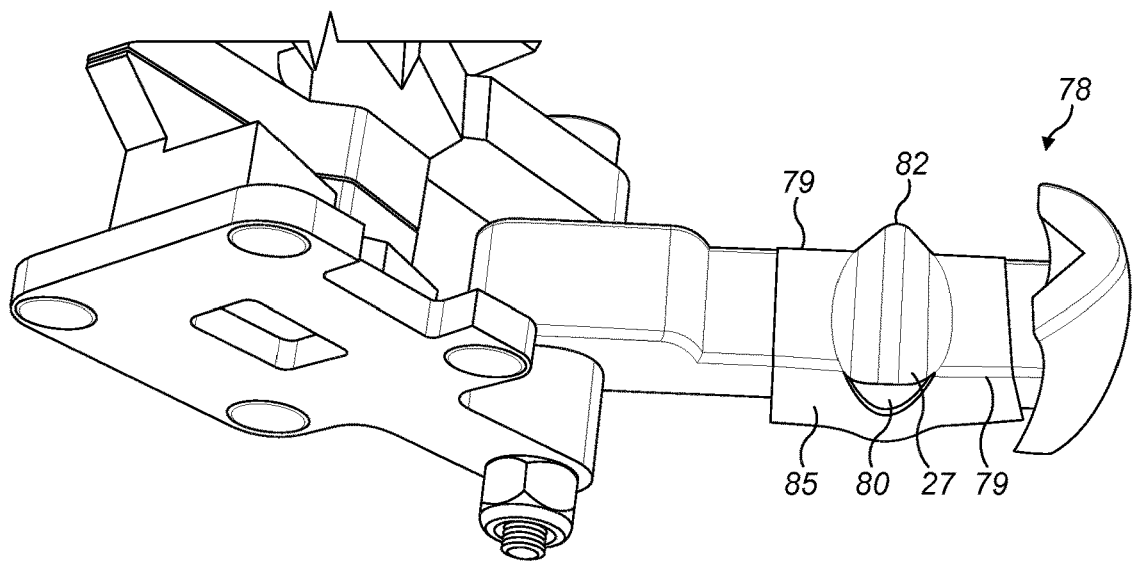
FIG. 11 shows the prototype jig of FIG. 11 after blister opening, in which two large apertures have been formed in the blister.

Although the images in FIGS. 10 and 11 depict a unit dose device, the actual opening mechanism of folding and popping open is the same for a multi dose device, which is why the demonstration jig 78 has been mentioned here.

During inhalation, when a user inhales through the mouthpiece 18, an airflow through the blister 28 via the two openings 80, 82 is generated to entrain the dose contained therein and carry it out of the blister and, via the mouthpiece 18, into the user's airway. No foil flaps are created that could hinder the flow of powder laden air out of the opened blister 28.

A free end of each fold member 64 may be bevelled. This shaping helps the applied folding pressure be transmitted gradually to the blister 28 as the blister folding element 62 moves from the first to the second position, resulting in a more controlled formation of the openings 80, 82. Bevelled ends help to reduce the overall opening force required of the user.

As shown in FIG. 9, an unfolding member 84 is mounted within the housing 12, preferably near to the blister strip drive member. The unfolding member 84 is located downstream of the blister opening position 20 and upstream of the second compartment 26. The purpose of the unfolding member 84 is to return two folded portions 85 of a recently opened blister 28 back to, or substantially to, an original, unfolded condition. This facilitates a tighter recoiling of the used portion of the blister strip 16 because the folded sections 85 would otherwise hinder recoiling.

The unfolding member 84 is best seen in FIG. 12. A body 86 of the unfolding member 84 is generally cubic. It has a concavely arcuate first (i.e. upper, as viewed in FIG. 12) surface 88 and a planar second (i.e. lower) surface 90 opposing the first surface 88. The curvature of the first surface 88 is perpendicular to the direction of travel of the blister strip 16 during indexing. The body 86 also has a leading third surface 92, which is where the used blister strip 16 approaches the unfolding member 84, and a trailing fourth surface 94, which is where the used blister strip 16 leaves the unfolding member 84. Arrow 95 indicates the direction of travel of the blister strip. Two wings 96, 98 extend laterally outwards from the body 86, with a specific profile designed to unfold folded portions 85 of opened blisters 28. Each wing is part-helical between the leading surface 92 of the body 86 and the trailing surface 94. Each wing 96, 98 blends through ninety degrees, twisting from near vertical to horizontal in a semi-spiral. This results in the formation of a contact surface 100 and a non-contact surface 102 for each wing 96, 98. The two folded portions 85 of each folded blister 28 glide over the contact surfaces 100 during use, starting at the leading surface 92 and by the time the blister 28 (whilst still remaining part of the blister strip 16) has reached the trailing surface 94 the folder portions 85 have been lifted due to the helical nature of the two wings 96, 98.

Many modifications and variations of the invention falling within the terms of the following claims will be apparent to those skilled in the art and the foregoing description should be regarded as a description of the preferred embodiment only.

The invention claimed is:

1. A dry powder inhaler comprising
a housing defining a chamber,
a blister strip comprising a plurality of blisters, each blister of said plurality of blisters containing a dose of medicament for inhalation by a user, each blister of said plurality of blisters comprising a blister lid attached to a blister bowl, the blister strip being disposed inside the chamber,
an actuator,
an indexing system configured to sequentially move each blister of said plurality of blisters into a blister opening position in response to movement of the actuator, said indexing system comprising
a blister strip drive member rotatably mounted in the chamber, said blister strip drive member comprising
an indexing wheel, the indexing wheel comprising a plurality of blister seats and two radially extending and spaced apart major, planar surfaces, each blister seat of said plurality of blister seats configured to support a central portion of the blister bowl of any one of the plurality of blisters, each blister seat of said plurality of blister seats being equi-angularly spaced apart about an axis of rotation of the indexing wheel, and each blister seat of said plurality of blister seats having two edges on two, respective opposing sides of the blister seat corresponding to said two radially extending and spaced apart major, planar surfaces such that two, respective spaced apart portions of the blister bowl are not supported by the blister seat,
a mouthpiece through which the dose of medicament is inhaled by the user, and
a blister opening device, the blister opening device comprising
a blister folding element comprising two pairs of spaced apart fold members, wherein the blister folding element is co-operable with the indexing wheel, and
wherein the blister folding element is movable relative to the indexing wheel between a first position, permitting movement of said blister into or onto one of the plurality of blister seats, wherein the two pairs of spaced apart fold members are not disposed on either of said two radially extending and spaced apart major, planar surfaces of the indexing wheel, and a second, burst, position in which the blister folding element has co-operated with the indexing wheel to move the two pairs of spaced apart fold members to be contiguous along one of said two radially extending and spaced apart major, planar surfaces to contact the two, respective spaced apart portions of the blister bowl to produce two spaced apart openings in the blister, each opening extending along a circumference of the blister bowl, beginning and terminating at points located on a fold line such that, when the user inhales through the mouthpiece, an airflow through the blister via the two spaced apart openings is generated to entrain the dose contained therein and carry it out of the blister and via the mouthpiece into the user's airway.

2. The dry powder inhaler of claim 1, wherein the blister folding element is slidable relative to the indexing wheel.

3. The dry powder inhaler of claim 1, wherein each blister seat of the plurality of blister seats comprises a central portion which has a truncated geometric shape, each fold line being one edge of truncation.

4. The dry powder inhaler of claim 1, wherein a longitudinal extent of each blister seat of said plurality of blister seats is arranged perpendicularly to a direction of travel of the blister strip during indexing.

5. The dry powder inhaler of claim 1, wherein each blister seat of said plurality of blister seats comprises a raised feature configured to cause an indentation at a base of the blister bowl for internally pressurising the blister.

6. The dry powder inhaler of claim 1, wherein the actuator is an actuating lever and wherein said actuating lever is pivotally mounted to the housing.

7. The dry powder inhaler of claim 6, wherein said actuating lever is configured to operate in a stroke, and wherein the actuating lever is configured to cause blister indexing during a first portion of its stroke, and to cause blister folding during a second and subsequent portion of its stroke.

8. The dry powder inhaler of claim 1, wherein the actuator is a cap, and wherein said cap is pivotally mounted to the housing.

9. The dry powder inhaler of claim 1, further comprising a deagglomeration chamber configured to deagglomerate a powder from each blister of said plurality of blisters when opened.

10. The dry powder inhaler of claim 1, further comprising an unfolding member configured to return folded portions of each blister of said plurality of blisters back to its original unfolded conditions after each blister of said plurality of blisters has been folded.

11. The dry powder inhaler of claim 1, wherein the blister strip comprises two longitudinal edges, and wherein each longitudinal edge comprises a series of spaced apart fold ears which extend laterally outwardly from said longitudinal edge.

\* \* \* \* \*